United States Patent [19]
Grandgeorge et al.

[11] Patent Number: 5,346,992
[45] Date of Patent: Sep. 13, 1994

[54] PROCESS FOR ISOLATING HUMAN ALBUMIN FROM SUPERNATANT IV, IN PARTICULAR IV-4, OR FROM COHN'S FRACTION V OR FROM AN ANALOGOUS SUPERNATANT OR FRACTION

[75] Inventors: Michel G. J. Grandgeorge, Vaugneray; Jean-Luc B. Veron, Sourcieux-les-Mines; Pierre L. J. Fournier, Lyons, all of France

[73] Assignee: Pasteur Merieux Serums et Vaccins, France

[21] Appl. No.: 832,081

[22] Filed: Feb. 6, 1992

[30] Foreign Application Priority Data

Feb. 7, 1991 [FR] France .................. 91 01365

[51] Int. Cl.$^5$ .................. C07K 3/00; B01D 15/00
[52] U.S. Cl. .................. 530/364; 530/362; 530/363; 530/380; 530/416; 530/417; 210/263; 210/290; 210/656; 210/660; 210/666
[58] Field of Search ........... 530/364, 362, 363, 380, 530/416, 417; 210/263, 290, 656, 660, 666

[56] References Cited

U.S. PATENT DOCUMENTS

| | | | |
|---|---|---|---|
| 4,043,997 | 8/1977 | Schroeder | 530/364 |
| 4,086,222 | 4/1978 | Lindquist et al. | 530/364 |
| 4,228,154 | 10/1980 | Fisher et al. | 530/364 |
| 4,675,384 | 6/1987 | Dromard et al. | 530/364 |

FOREIGN PATENT DOCUMENTS

| | | | |
|---|---|---|---|
| 367220 | 10/1989 | European Pat. Off. | C07K 3/20 |
| 0367220 | 9/1990 | European Pat. Off. | C07K 3/20 |

OTHER PUBLICATIONS

Grandgeorge et al, *Chemical Abstracts*, vol. 114, Reference No. 12182W (Fr. Demande Fr. 2,630,115), 1,14,91.

Bulik et al, *Chemical Abstracts*, vol. 110, Reference No. 150957W (Czech. CS 248,241), 1989.

Lobunets et al, *Chemical Abstracts*, vol. 89, Reference No. 125651g (Ukr. Biochem. Zh. 1978, 50(4) 512–16) 1978.

Schneider et al, *Chemical Abstracts*, vol. 87, Reference No. 35427t, 1977.

Pokorny et al, *Chemical Abstracts*, vol. 96, Reference No. 168771h (Czech. CS. 194,957), 1982.

J. F. Stoltz et al, Biotechnology of Plasma Proteins, Chromatographic Purification of Human Albumin Technical and Economic Aspects, pp. 191–200, Colloque INSERM.

C. Treps et al., Vox Sang 35, 1978, pp. 143–148, Different Fates of Hepatitis B Virus Markers during Plasma Fractionation.

J. F. Stoltz et al., Bio-sciences 6 (4), 1987, pp. 103–106, Purification chromatographique de l'albumine plasmatique humaine a l'echelle pilote.

*Primary Examiner*—Michael G. Wityshyn
*Assistant Examiner*—Abdel A. Mohamed
*Attorney, Agent, or Firm*—Larson and Taylor

[57] ABSTRACT

The process for isolating albumin from supernatant IV, and in particular IV-4, or from COHN's fraction V or from a plasma supernatant or fraction of analogous composition derived from an alcoholic or nonalcoholic fractionation, comprises one step on a hydrophilic anion exchange column with binding of albumin to the column, and then elution, and one step on a hydrophobic anion exchange column. Albumin thus obtained having a purity >99% by cellulose acetate electrophoresis, being free from impurities detected by crossed immunoelectrophoresis and free from polymers.

9 Claims, No Drawings

PROCESS FOR ISOLATING HUMAN ALBUMIN FROM SUPERNATANT IV, IN PARTICULAR IV-4, OR FROM COHN'S FRACTION V OR FROM AN ANALOGOUS SUPERNATANT OR FRACTION

The invention relates to a process for isolating human albumin from supernatant IV, in particular IV-4, or from COHN's fraction V or from a plasma supernatant or fraction of analogous composition derived from an alcoholic or non-alcoholic fractionation, by ion exchange chromatography steps.

French Patent Application FR-A-2,327,256 describes the preparation of albumin from immunoglobulin-free plasma which may be COHN's fraction V. The purification is carried out successively on a hydrophilic anion exchanger onto which albumin binds and a hydrophilic cation exchanger. This process leads to an albumin of average purity (>96%) and containing less than 3.5% of polymers.

Patent US-A-4,228,154 also describes a process for preparing albumin from COHN's supernatant II+III, this fraction being freed from immunoglobulins. The process comprises, firstly, a gel filtration in order to remove alcohol and residual salts and then an adsorption of the lipoproteins on silica and finally two chromatographic steps on a hydrophilic anion exchanger and a hydrophilic cation exchanger. The albumin obtained has a relatively high electrophoretic purity ranging between 96.9% and 98.9%. In this process, the albumin is never bound to the chromatographic support.

In European Patent Application EP-A-0,367,220, in which COHN's fraction V is used as starting material, the cation exchange chromatographic step is omitted. The process described comprises the passage through a weak or strong hydrophilic anion exchange column onto which albumin does not bind and the product obtained still contains polymers (3%).

French Patent Application FR-A-2,543,448 describes a process for obtaining an albumin of high purity ($\geq$99% by electrophoresis) using, this time, as starting material a plasma which is crude or which is freed from the cryoprecipitate which has been subjected only to an initial clarification intended to remove the salts and the euglobulins. The process requires, nevertheless, complex chromatographic fractionation steps using at least one anion exchanger and one cation exchanger, and a hydrophobic-type support, which may be one of the preceding ion exchangers, and, in particular, a hydrophilic anion exchanger onto which albumin binds, before being eluted, a hydrophobic anion exchanger and a cation exchanger.

The object of the present invention is to provide a process for purifying albumin which yields an albumin of purity greater than 99% and which is polymer-free, while preserving the viral safety provided by COHN's alcoholic fractionation.

The Applicant has surprisingly found that it was possible to obtain such an albumin of very high electrophoretic purity and which is polymer-free by using as starting material, supernatant IV, and in particular IV-4, or COHN's fraction V (dissolved), or a plasma supernatant or fraction of analogous composition derived from an alcoholic or non-alcoholic fractionation, while maintaining at a low level the costs of the instrumentation and of its operation.

The object of the invention is a process for isolating albumin from the above supernatants or fractions, comprising two ion exchange chromatographic steps, one step on a hydrophilic anion exchange column with binding of albumin to the column, and then elution, and one step on a hydrophobic anion exchange column. The anion exchangers may be either weak or strong.

The steps of the process are preferably carried out in this order but may also be carried out in the reverse order provided that there is an increase in the volume of the hydrophobic anion exchanger.

This process makes it possible to obtain an albumin of very high purity, greater than 99% by cellulose acetate electrophoresis, which is free from impurities detected by crossed immunoelectrophoresis and which is very stable as it is free from substantial amounts of polymers (<1% after legal pasteurization for 10 h at 60° C.). The yield of the chromatographic purification is higher than 90% with respect to the proteins to be processed.

Preferably, the hydrophilic anion exchange column is a DEAE-SPHERODEX ® chromatographic support column (porous silica beads coated with a dextran hydrophilic polymer bearing DEAE tertiary amine groups; weak anion exchanger, hydrophilic) and the hydrophobic anion exchange column is a QMA-SPHEROSIL ® chromatographic support column (porous silica beads coated with a polyvinyltoluene hydrophobic polymer bearing QMA quaternary ammonium groups; strong anion exchanger, hydrophobic).

More generally, chromatographic supports may be used which are based on porous silica coated with a polymer which is either hydrophilic (dextran derivative for example) or hydrophobic (polyvinyltoluene derivative for example).

Supports which are equivalent to the above supports may also be used, in particular:

a) supports based on porous inorganic silica coated with other polymers:
  hydrophilic polymers: gelose, hydrophilic polyvinyls, hydrophilic polyacrylamides or equivalent polymers which are non-toxic and non-denaturing for the proteins,
  hydrophobic polymers: the same as above but made hydrophobic by grafting or co-crosslinking of hydrophobic groups such as styrene and hexyl groups and, generally, aliphatic chains and aromatic groups offering a hydrophobic character, it being understood that the polymers should be non-toxic and non-denaturing for the proteins, b) supports based on hydrophilic organic polymers or made hydrophobic as above:
  polysaccharides (cellulose, dextran, gelose and the like)
  polyvinyl
  polyacrylamide
  mixed polyacrylamide-gelose
  or equivalents which are non-toxic and non-denaturing for the proteins.

The above polymers should bear chemical groups which give them the anion exchange properties according to the intended use.

The object of the present invention is also an albumin obtained according to the process conforming to the invention.

The invention will now be described in greater detail by means of exemplary embodiments of the invention.

EXAMPLE 1

6 kg of COHN's fraction V corresponding to 61.4 litres of citrated plasma at about 50 g/l of total proteins are dissolved in apyrogenic deionized water at +4° C. The solution is adjusted to a pH of 5.25 and a resistivity of 1500 Ωcm. The protein level is 23.9 g/l. The solution is filtered at room temperature on a DEAES-PHERODEX ® column with 9 kg of support preequilibrated in 10 mM sodium phosphate buffer, pH 5.25. After rinsing the column with the same buffer, the albumin is eluted using a 25 mM solution of sodium acetate buffer, pH 4.7. 61.3 litres of albumin solution at 21.1 g/l of proteins are obtained. This solution is then filtered at room temperature on a column with 4 kg of QMA-SPHEROSIL ® preequilibrated in a 25 mM solution of sodium acetate buffer, pH 4.7. The filtrate is adjusted to a pH of 6.5, dialyzed in ultrafiltration membranes with a 10 kD cutoff against 6 g/l NaCl to remove the sodium acetate and then concentrated to more than 200 g/l of proteins in the same ultrafiltration membrane. The solution is then adjusted as follows: proteins to 200 g/l and stabilizers: sodium caprylate 2.7 g/l, N-acetyltryptophan 4 g/l, sodium 145 meq/l, Tween 80 15 mg/l and pH 6.95. It is then pasteurized for 10 h at 60° C. and subjected to final checks. The overall yield is 21.7 g of purified albumin per litre of initial plasma. It represents 91% of the fraction V proteins. Its purity, by cellulose acetate electrophoresis, is 100% and the polymer level is 0%. No impurity is detectable by crossed immunoelectrophoretic analysis.

EXAMPLE 2

142.5 litres of COHN's filtrate IV-4, corresponding to 70 litres of citrated plasma at about 50 g/l of total proteins, are ½-diluted in apyrogenic deionized water at +4° C. This solution is dialyzed at a pH of 5.5 against apyrogenic deionized water so as to obtain a resistivity of 1500 Ωcm for a pH adjusted to 5.25. The solution is then treated as in Example 1 on a column with 9 kg of DEAE-SPHERODEX ® and a column with 4 kg of QMASPHEROSIL ®, and then analyzed after pasteurization as above.

The final yield is 24.3 g of purified albumin per litre of initial plasma. It represents 94% of the supernatant IV-4 proteins. Its purity, by cellulose acetate electrophoresis, is 100% and the polymer level is 0%. No impurity is detected by crossed immunoelectrophoresis.

The amount of chromatographic support used in this example is 3.2 kg of DEAE-SPHERODEX ® per 25 l of plasma and 1.4 kg of QMA-SPHEROSIL ® per 25 l of plasma. The process of the invention does not increase the amounts of chromatographic support in comparison with prior processes using as starting material a COHN's supernatant or fraction and, in comparison with the prior process of French Patent Application FR-A-2,543,448, a substantial saving of chromatographic support is achieved due, in particular, to the omission of the cation exchanger and, consequently, of the required amounts of buffers and eluents, while yielding an albumin of comparable electrophoretic purity.

The process according to the invention also makes it possible to reduce the investment and maintenance costs linked to the number of chromatographic steps and therefore to the number of columns, compared with Application FR-A-2,543,448 while offering a product, at least, of equal quality.

Because of its high purity, this albumin may, in addition to clinical use, be used as an adjuvant or stabilizing agent for high specific activity, high purity biological products such as highly purified coagulation factors. In particular, it may be used as a component of defined culture media, without animal serum, for producing recombinant molecules with therapeutic activity or as excipient in the final pharmaceutical formulations of these molecules.

We claim:

1. A process for isolating albumin having a purity greater than 99% with a polymer content lower than 1%, from a supernatant IV, or from COHN's fraction V derived from an alcoholic fractionation, comprising two anion exchange chromatographic steps, wherein one step is carried out on a hydrophilic anion exchange column with binding of albumin to the column followed by elution, and the other step is carried out on a hydrophobic anion exchange column.

2. The process as claimed in claim 1, wherein the supernatant IV or the COHN's fraction V is passed through a chromatographic column containing porous silica beads coated with a hydrophilic polymer and then through a chromatographic column containing porous silica beads coated with a hydrophobic polymer.

3. The process as claimed in claim 7, wherein the hydrophilic polymer is a dextran derivative and the hydrophobic polymer is a polyvinyltoluene derivative.

4. The process as claimed in claim 3, wherein the hydrophilic polymer is a dextran bearing tertiary amine groups and the hydrophobic polymer is a polyvinyltoluene bearing quaternary ammonium groups.

5. The process as claimed in claim 2, wherein the hydrophilic polymer is selected from the group consisting of agarose, hydrophilic polyvinyls and hydrophilic polyacrylamides.

6. The process as claimed in claim 2, wherein the hydrophobic polymer is selected from the group consisting of agarose, polyvinyls and polyacrylamides made hydrophobic by grafting or co-crosslinking of hydrophobic groups.

7. The process as claimed in claim 1, wherein the supernatant IV-4 or the COHN's fraction V is passed through columns containing a hydrophilic or hydrophobic organic polymer.

8. The process as claimed in claim 7, wherein the polymer is selected from the group consisting of polysaccharides, polyvinyls, polyacrylamides and mixed polyacrylamide-agarose.

9. A process for isolating albumin having a purity essentially of 100% with a polymer content essentially of 0%, from a supernatent IV, or from COHN's fraction V, comprising two anion exchange chromatographic steps, wherein one step is carried out on a hydrophilic anion exchange column with binding of albumin to the column, followed by elution, and the other is carried out on a hydrophobic anion exchange column.

* * * * *

UNITED STATES PATENT AND TRADEMARK OFFICE
CERTIFICATE OF CORRECTION

PATENT NO. : 5,346,992

DATED : September 13, 1994

INVENTOR(S) : GRANDGEORGE ET AL.

It is certified that error appears in the above-identified patent and that said Letters Patent is hereby corrected as shown below:

The Title page, item [75] should read:

Michel G.J. Grandgeorge, Vaugneray; Jean-Luc B. Veron, Sourcieux-les-Mines; Pierre L.J. Fournier, Lyon, all of France Signed and Sealed this Second Day of May, 1995

Attest:

BRUCE LEHMAN

Attesting Officer     Commissioner of Patents and Trademarks